United States Patent [19]

Tanner et al.

[11] Patent Number: 5,019,375

[45] Date of Patent: May 28, 1991

[54] LOW RESIDUE ANTIPERSPIRANT CREAMS

[75] Inventors: Paul R. Tanner; Randolph G. Nunn, Jr., both of Cincinnati, Ohio; John P. Luebbe, Lawrenceburg, Ind.

[73] Assignee: The Procter & Gamble Company, Cincinnati, Ohio

[21] Appl. No.: 323,524

[22] Filed: Mar. 14, 1989

[51] Int. Cl.$^5$ .................. A61K 7/32; A61K 7/34; A61K 7/36; A61K 7/38

[52] U.S. Cl. ................... 424/66; 424/DIG. 5; 424/67; 424/68

[58] Field of Search ........................... 424/66, 68

[56] References Cited

U.S. PATENT DOCUMENTS

| | | | |
|---|---|---|---|
| 3,255,082 | 6/1966 | Barton et al. | 424/68 |
| 3,968,203 | 7/1976 | Spitzer et al. | 424/47 |
| 4,083,956 | 4/1978 | Shelton | 424/66 |
| 4,229,432 | 10/1980 | Geria | 424/68 |
| 4,265,878 | 5/1981 | Keil | 424/68 |
| 4,268,499 | 5/1981 | Keil | 424/68 |
| 4,425,328 | 1/1984 | Nabial | 424/68 |
| 4,548,808 | 10/1985 | Chavkin | 424/67 |
| 4,719,103 | 1/1988 | Krevald et al. | 424/66 |
| 4,724,139 | 2/1988 | Palinczar | 424/66 |
| 4,749,569 | 6/1988 | Gianino et al. | 424/66 |
| 4,777,035 | 10/1988 | Shin | 424/66 |
| 4,840,789 | 6/1989 | Orr et al. | 424/66 |
| 4,853,214 | 8/1989 | Orr et al. | 424/66 |
| 4,863,721 | 9/1989 | Beck et al. | 424/66 |

FOREIGN PATENT DOCUMENTS

| | | | |
|---|---|---|---|
| 28853 | 5/1981 | European Pat. Off. | 424/68 |
| 135315 | 3/1985 | European Pat. Off. | 424/68 |

OTHER PUBLICATIONS

Ser. No. 323,523, Tanner, Nunn and Luebbe, 3/14/89.

*Primary Examiner*—Dale R. Ore
*Attorney, Agent, or Firm*—Steven J. Goldstein; Leonard W. Lewis

[57] ABSTRACT

Antiperspirant cream compositions, which exhibit reduced residue on the skin and excellent cosmetics and aesthetics, as well as good composition stability over time, are claimed. These compositions, which may be formulated to have relatively high viscosities, include a volatile silicone material, a particulate antiperspirant active, a clay thickening agent, an activator for the clay thickening agent, and a non-volatile paraffinic hydrocarbon fluid, such as mineral oil or branched chain $C_{16}$–$C_{68}$ hydrocarbons. A method of treating or preventing perspiration in humans using these compositions is also claimed.

10 Claims, No Drawings

LOW RESIDUE ANTIPERSPIRANT CREAMS

TECHNICAL FIELD

The present invention relates to antiperspirant compositions in cream form which provide good antiperspirant efficacy together with reduced residue on the skin, excellent cosmetics and aesthetics, and good composition stability over time. These compositions may be formulated to have very high viscosities.

BACKGROUND OF THE INVENTION

Compositions designed to stop or reduce the flow of perspiration are well-known in the cosmetic and chemical literature. Antiperspirants typically contain an astringent material, such as an astringent aluminum or zirconium salt. These compositions are designed to deliver the active to the skin in an effective form, while being cosmetically acceptable to the user.

A variety of methods have been used to apply antiperspirant compositions to the skin. For example, spray, roll-on, cream, and stick compositions are commonly used. Such formulations are described in Plechner, "Antiperspirants and Deodorants", Cosmetics, Science and Technology; 2:373-416 (Balsam & Sagarin, Ed., 1972).

A variety of cream-type formulations are known. For example, cream emulsions are described in U.S. Pat. No. 4,268,499, Keil, issued May 19, 1981. Cream suspensions are described in European Patent Application 28,853, Beckmeyer et al., published May 20, 1981. Anhydrous creams in gel form are described, for example, in U.S. Pat. No. 4,083,956, Shelton, issued Apr. 11, 1978, and European Patent Application 135,315, Kasat, published Mar. 27, 1985. However, cream compositions present particular formulation and use problems and, as a result, have been less popular than other antiperspirant product forms. For example, some cream compositions may be sticky and produce aesthetically undesirable levels of white chalky residue on the skin after use. Creams may also be messy and otherwise difficult to apply. Special packages and dispensers have been designed to reduce such application negatives. In spite of this, the residue and aesthetics problems generally tend to make creams a less desirable form for antiperspirant compositions.

It has now been found that the antiperspirant creams of the present invention, which utilize specifically defined non-volatile paraffinic hydrocarbon fluids together with a volatile silicone material, a particulate antiperspirant active, a clay thickening agent, and an activator for the clay, provide effective antiperspirant performance together with reduced residue upon application to the skin, reduced residue on the skin after dry-down, excellent cosmetics and aesthetics, and improved composition stability over time. The present invention may also provide a benefit in terms of improved delivery and substantivity of perfumes included in the compositions. If desired, these compositions may be formulated to have very high viscosities.

Mineral oil has been taught in the art for use in water-containing emulsion-type deodorant sticks (e.g., U.S. Pat. No. 3,255,082, Barton et al., issued June 7, 1966), in aerosol deodorants (e.g., U.S. Pat. No. 3,968,203, Spitzer et al., issued July 6, 1976), and in deodorant creams (e.g., U.S. Pat. No. 4,083,956, Shelton, issued Apr. 11, 1978). See also European Patent Application 28,853, Beckmeyer et al., published May 20, 1981 (mineral oil as a non-volatile emollient in liquid antiperspirant compositions).

U.S. Pat. No. 4,424,328, Nabial, issued Jan. 19, 1984, describes deodorant sticks containing an antiperspirant active, a volatile cyclic silicone emollient, a clay suspending agent, and an activator for the clay. These compositions may optionally include emollients, such as 2-ethylhexyl palmitate. U.S. Pat. No. 4,265,878, Keil, issued May 5, 1981, describes emulsion-type deodorant sticks containing an antiperspirant active dispersed in a solid matrix which includes a volatile water-insoluble liquid. Useful volatile liquids include cyclic polysiloxanes and paraffinic hydrocarbons. Clays are not taught to be included in these compositions. U.S. Pat. No. 4,229,432, Geria, issued Oct. 21, 1980, describes the use of certain waxy materials to keep the active components dispersed in an antiperspirant stick composition. Straight and branched-chain paraffinic hydrocarbon waxes are disclosed. U.S. Pat. No. 4,724,139, Palinczar, issued Feb. 9, 1988, describes antiperspirant sticks which include 5-80% of a volatile isoparaffin liquid, 5-60% of a water-insoluble wax, such as castor wax, and 8-60% of a particulate antiperspirant active. There is no disclosure of clays or clay activators in these compositions. Further, the branched chain hydrocarbons utilized in the Keil and Palinczar patents are volatile, as opposed to the non-volatile materials required in the present invention. These prior art products, which relate to deodorant sticks, would tend to leave a visible residue on the skin after use.

SUMMARY OF THE INVENTION

The present invention provides antiperspirant cream compositions, having a penetration force value of from about 60 to about 500 grams, comprising:

(a) from about 20% to about 70% of volatile silicone material;

(b) from about 5% to about 35% of a particulate antiperspirant active;

(c) from about 3% to about 10% of a clay thickening agent;

(d) from about 0.1% to about 5% of an activator for said clay thickening agent; and (e) from about 5% to about 40% of a non-volatile paraffinic hydrocarbon fluid selected from the group consisting of mineral oils, branched-chain $C_{16}$-$C_{68}$ hydrocarbon emollients, and mixtures thereof.

Preferred compositions additionally contain from about 0.5% to about 5% of a non-clay thickener, such as castor wax. The present invention also encompasses a method of treating and preventing perspiration in humans utilizing these compositions.

DETAILED DESCRIPTION OF THE INVENTION

The antiperspirant cream compositions of the present invention comprise a volatile silicone material, a particulate antiperspirant active, a clay thickening agent, an activator for the clay thickening agent, and a non-volatile paraffinic hydrocarbon fluid. The components to be included in these creams must be "cosmetically acceptable", i.e., safe for human use via topical application and aesthetically acceptable at the levels encompassed by the present invention, at a reasonable risk/benefit ratio.

The compositions encompass any semi-solid formulation that is suitable for depositing antiperspirant material on human skin. The creams of this invention have a penetration force value of from about 60 g to about 500 g, preferably from about 100 g to about 300 g, at 25° C. and at 50% relative humidity, as measured with a Stevens Texture Analyzer, manufactured by C. Stevens & Sons, Ltd. This value is the force required to move a standardized 1.5 cm diameter disc through the product, for a distance of 5 mm, at a rate of 2 mm/second. It is a unique benefit of the present invention that effective, aesthetic, low residue compositions may be formulated having high viscosities.

The components used in the present invention are described in detail below. As used herein, all percentages and ratios are by weight unless otherwise specified.

VOLATILE SILICONE MATERIAL

The compositions of the present invention contain from about 20% to about 70%, preferably from about 20% to about 50%, of a volatile silicone material. As used in this context, "volatile" refers to those materials which have measurable vapor pressure at ambient conditions. Such volatile silicones may be cyclic or linear. A description of various volatile silicones is found in Todd et al., "Volatile Silicone Fluids for Cosmetics", Cosmetics and Toiletries, 91:27-32 (1976), incorporated herein by reference.

Preferred volatile silicone materials include those having from about 3 to about 7, preferably from about 4 to about 5, silicon atoms. Cyclic volatile silicones are preferred for use herein and include those having the formula:

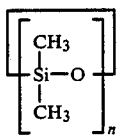

wherein n is from about 3 to about 7. Linear volatile silicone materials include those having the formula:

wherein n is from about 1 to about 7. Linear volatile silicones generally have viscosities of less than about 5 centistokes at 25° C., whereas the cyclic silicones have viscosities of less than about 10 centistokes. Examples of volatile silicones useful in the present invention include: Dow Corning 344, Dow Corning 345, and Dow Corning 200 (commercially available from Dow Corning Corp.); GE 7207 and 7158 (commercially available from General Electric Co.); and SWS-03314 (commercially available from SWS Silicones Corp.).

PARTICULATE ANTIPERSPIRANT MATERIAL

The compositions of the present invention also include from about 5% to about 35%, preferably from about 10% to about 30%, of a particulate antiperspirant material. These weight percentages are calculated on an anhydrous metal salt basis (exclusive of glycine, the salts of glycine, or other complexing agents). The particulate antiperspirant material preferably has particle sizes ranging from about 1 to about 100 microns, more preferably from about 1 to about 50 microns. They may be impalpable or microspherical in form and, preferably, have a high bulk density (e.g., greater than about 0.7 g/cm³).

The particulate antiperspirant materials utilized in the present invention comprise any compound or composition or mixtures thereof having antiperspirant activity. Astringent metallic salts are preferred antiperspirant materials for use herein, particularly the inorganic and organic salts of aluminum, zirconium and zinc, as well as mixtures thereof. Particularly preferred are the aluminum and zirconium salts, such as aluminum halides, aluminum hydroxy halides, zirconyl oxide halides, zirconyl hydroxy halides, and mixtures thereof.

Preferred aluminum salts include those having the formula:

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "⅔ basic chlorhydroxide", wherein a=4. Processes for preparing aluminum salts are disclosed in U.S. Pat. Nos. 3,887,692, Gilman, issued June 3, 1975; 3,904,741, Jones et al., issued Sept. 9, 1975; 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, also incorporated herein by reference.

Zirconium salts are also preferred for use in the antiperspirant creams of the present invention. Such salts have the general formula:

$$ZrO(OH)_{2-a}Cl_a \cdot xH_2O$$

wherein a is from about 1.5 to about 1.87; x is from about 1 to about 7; and wherein a and x may have non-integer values. These zirconium salts are described in Belgian Patent 825,146, Schmitz, issued Aug. 4, 1975, incorporated by reference herein. Particularly preferred zirconium salts are those complexes which additionally contain aluminum and glycine, commonly known as ZAG complexes. Such ZAG complexes contain aluminum chlorhydroxide and zirconyl hydroxy chloride of the formulae described above. Such ZAG complexes are described in U.S. Pat. No. 3,679,068, Luedders et al., issued Feb. 12, 1974, and U.S. Pat. No. 4,120,948, Shelton, issued Oct. 17, 1978, both of which are incorporated by reference herein.

Also useful herein are the ZAG complexes disclosed in Great Britain Patent Application 2,144,992, Callaghan et al., published Mar. 20, 1985, incorporated herein by reference. These ZAG actives, when analyzed by high pressure gel permeation chromatography, exhibit a distribution pattern having 4 or more successive peaks or "bands", where the height ratio of bands IV to III is greater than about 2:1. Most preferred are the ZAG actives which have a total area under the curve of bands I and II of less than about 10%, preferably less than about 5%, more preferably less than about 2%, and most preferably less than about 1%.

CLAY THICKENING AGENT

The present invention also includes from about 3% to about 10% of a clay thickening agent, or a mixture of such thickening agents, particularly hydrophobically-treated clays. The thickening agents useful herein include hydrophobically-treated montmorillonite clays, e.g., bentonites and hectorites. Many such clay thickening agents are commercially available. They include, for example, Bentone 38 (hectorite) and Bentone 34 (bentonite), commercially available from NL Industries, Inc., and Tixogel (bentonite), commercially available from United Catalyst, Inc.

The hectorite and bentonite clay minerals described above are expandable (swellable), 3-layer clays, in which a sheet of aluminum/oxygen atoms or magnesium/oxygen atoms lies between 2 layers of silicone/oxygen atoms, i.e., aluminosilicates and magnesium silicates, having an ion exchange capacity of at least about 50 meq/100 g of clay, and preferably at least about 60 meq/100 g of clay. The term "expandable", as used to describe the clays herein, relates to the ability of the layered clay structures to be swollen or expanded on contact with water. Such hectorite and bentonite clays are described in Grim, Clay Minerology (2nd Ed.),pp 77-79 (1968), and VanOlphen, An Introduction to Clay Colloid Chemistry (2nd Ed.), pp 64-76 (1977), both of which are incorporated by reference herein.

The clay minerals employed in the compositions of the present invention contain exchangeable cations including, but not limited to, protons, sodium ions, potassium ions, calcium ions, magnesium ions, lithium ions, and the like. It is customary to distinguish between clays on the basis of one cation predominantly or exclusively absorbed. For example, a sodium clay is one in which the absorbed cation is predominantly sodium. As used herein, the term "clay", such as a hectorite clay, includes all the various exchangeable cation variants of that clay, e.g., sodium hectorite, potassium hectorite, lithium hectorite, magnesium hectorite, calcium hectorite, etc.

The clay minerals employed in the present invention are made hydrophobic by treating them with a cationic surfactant material. A preferred cationic surfactant is a quaternary ammonium cationic surfactant, such as ditallow dimethyl ammonium chloride.

THICKENING AGENT ACTIVATOR

The compositions of the present invention contain from about 0.1% to about 5% of an activator for the clay thickening agent to enable the hydrophobically-treated clay to suspend the antiperspirant active in the deodorant creams of the present invention. Such activating materials are well known in the art and include, for example, propylene carbonate, ethanol, methanol, and mixtures thereof.

NON-VOLATILE PARAFFINIC HYDROCARBON FLUID

A critical component of the antiperspirant creams of the present invention is the specifically selected non-volatile paraffinic hydrocarbon fluid. The compositions of the present invention include from about 5% to about 40%, preferably from about 10% to about 30%, of a non-volatile paraffinic hydrocarbon fluid. If the level of non-volatile hydrocarbon fluid is too low, the low residue benefits of the present invention are not seen; if the level of non-volatile hydrocarbon fluid is too high, the deodorant product tends to be too greasy, having undesirable aesthetics. As used in this context, the term "non-volatile" means that the hydrocarbon fluids used in the present invention have a boiling point of at least about 200° C. Further, the hydrocarbon fluids must be liquids at room temperature. The hydrocarbon fluids useful in the present invention include mineral oils and certain branched-chain hydrocarbons.

Mineral oils useful in the present invention are petroleum derivatives which are complex mixtures of paraffinic and naphthenic (cyclic) hydrocarbons. These include both "light" and "heavy" mineral oils, which are differentiated on the basis of the average molecular weight of the hydrocarbons included. The mineral oils useful herein have the following properties:

viscosity of from about 5 centistokes to about 70 centistokes at 40° C.;

density between about 0.82 and about 0.89 g/cm$^3$ at 25° C.;

flash point between about 138° C. and about 216° C.; and carbon chain length between about 14 and about 40 carbons.

The branched chain hydrocarbons useful in the present invention are highly branched non-volatile aliphatic liquids containing an average of from about 16 to about 68, preferably from about 16 to about 24, carbon atoms. If the compounds are not sufficiently branched, they will be waxes rather than the liquids required in the present invention. Materials containing 15 and fewer carbons tend to be too volatile for use in the present invention. Commercially available materials are mixtures of various branched chain compounds, rather than a single pure compound. Branched chain hydrocarbon fluids useful herein have the following properties:

density between about 0.79 and about 0.89 g/cm$^3$ at 20° C.;

boiling point greater than about 200° C.; and flash point between about 90° C. and about 200° C.

Preferred branched chain hydrocarbons are commercially available under the tradenames Permethyl (Permethyl Corporation) and Isopar (Exxon). In selecting a branched chain hydrocarbon material, its average carbon chain length must be considered to make certain that it falls within the ranges set forth herein. Particularly preferred materials include Permethyl 103A, which contains an average of about 24 carbon atoms, Permethyl 102A, which contains an average of about 20 carbon atoms, and Permethyl 101A, which contains an average of about 16 carbon atoms.

NON-CLAY THICKENER

Preferred antiperspirant creams of the present invention contain, in addition to the clay thickening agent, from about 0.5% to about 5% of a non-clay thickener. The addition of this non-clay thickener has a particularly beneficial effect in improving the product's viscosity, stability, and cosmetics. Such materials are well known in the art and include for example, castor wax, beeswax, spermaceti, carnauba, bayberry, candelilla, montan, ozokerite, ceresin, paraffin, synt waxes such as Fisher-Tropsch waxes, microcrystalline waxes, and mixtures thereof. A particularly preferred non-clay thickener is castor wax (commercially available under the tradenames Thixin E and Thixin R from NL Industries).

Another non-clay thickening material which may be used in the present invention is finely divided silica or "colloidal silica" which is comprised of micron to submicron sized silica particulates having high surface areas (preferably greater than about 100 square meters per gram of material). Preferably, the colloidal silica material is less than about 1 micron in size, and is most preferably a fumed silica. Colloidal silica materials are described in Hardy et al., "The Use of Fumed Silicas in Cosmetics", Cosmetic Technology 2:35 (1980), incorporated herein by reference. Useful colloidal silica materials include those marketed as Syloid silicas (manufactured by Davison Chemical Division of W. R. Grace), Cab-O-Sil (manufactured by Cabot Corp.), and Aerosil (manufactured by Degussa A.G.). Cab-O-Sil is a preferred commercially-available colloidal silica useful herein, having a surface area of from about 200 to about 400 square meters per gram.

The compositions of the present invention may also contain optional components which modify the physical characteristics of the vehicles or serve as "active" components when deposited on the skin in addition to the particulate antiperspirant active material. Additional active components include bacteriostats and fungistats. Optional components useful herein are described in U.S. Pat. No. 4,049,792, Elsnau, issued Sept. 20, 1977, and European Patent Application 28,853, Beckmeyer et al., published June 20, 1981, both incorporated herein by reference. The specific non-active components that may be useful herein will depend upon the characteristics (e.g., thickness, color, odor, skin-feel) that are desired for the particular composition being formulated. Such components include, for example, emollients, colorants, perfumes, and emulsifiers.

The antiperspirant cream compositions of the present invention may also optionally contain from about 0.5% to about 5% of a particulate hydrophilic polymer. These polymers assist in the removal of the antiperspirant residue from the skin during washing. Preferred hydrophilic polymers include cellulose ether polymers (cationic, neutral, and anionic), modified starches, polyamides (especially polyacrylamides), and polypeptides, as disclosed generally in Davidson, Handbook of Water-Soluble Gums and Resins, 1980. Preferably, the polymer is selected from nonionic cellulose ether polymers, such as alkylcelluloses (e.g., methylcellulose), hydroxyalkyl alkylcelluloses (e.g., hydroxypropyl methylcellulose, hydroxybutyl methylcellulose, ethyl-hydroxy ethylcellulose), hydroxy alkylcelluloses (e.g., hydroxyethylcellulose, hydroxypropylcellulose), and mixtures thereof. Most preferred are the hydroxy alkylcelluloses, especially hydroxyethylcellulose and hydroxypropylcellulose.

Another optional component which may be included in the antiperspirant creams of the present invention is a cosmetic powder or a mixture of such powders, incorporated at level of from about 0.5% to about 10%. In order to optimize the low residue benefits of the present invention, it may be useful, in certain compositions, to limit the total amount of particulates and powders (other than the antiperspirant active and the clay thickener) to no more than about 8% of the composition. Cosmetic powders useful herein include "inert spherical particulate materials" having a mean diameter of at least about 10 microns. Such inert particulate materials include, for example, polyolefins (such as polystyrene, polyethylene, and polypropylene), nylon, waxes, teflon, essentially water-insoluble cross-linked starches, and mixtures thereof. Other cosmetic powders useful herein include silicate powders (including talc, aluminum silicate and magnesium silicate), modified corn starches, metallic stearates, and mixtures thereof. Talc is described in Plotkin, "Cosmetic Talc", C. T. F. A. Cosmetic Journal 11:13–16 (1979), incorporated by reference herein. Commercially-available powders include, for example, Veecote (anhydrous aluminum silicate, commercially available from R. T. Vanderbilt Co., Inc.) and Dry Flo (aluminum starch succinate, commercially available from National Starch & Chemicals Co.).

The processes used for making the compositions of the present invention, as well as the equipment used in such processes, are well known to those skilled in the art. They may be batch processes (i.e., involving discrete processing steps) or continuous processes (i.e., wherein the product composition is passed between processing steps in essentially continuous increments). The process used for making the cream compositions of the present invention may be as simple as thoroughly mixing together all of the components. For example, in one method for making the compositions of the present invention, all of the ingredients, with the exception of the activator for the clay thickening agent, are combined and heated to a temperature of from about 35° C. to about 50° C. The specific temperature used will depend upon the characteristics of the particular components being mixed. The temperature selected may be the one necessary to activate the non-clay thickener, if one is utilized in the composition. The mixture is then allowed to cool to room temperature. The activator is added to the composition with high shear mixing or milling to form a stable cream product. Examples of high shear mixers which may be used in this process are well-known and include, for example, homogenizers and colloid mills. Specific essential and non-essential materials to be included in the present invention, and their levels, are selected to produce a cream of desired aesthetics and viscosity, which deposits a suitable amount of antiperspirant active on the skin during use. In making the compositions of the present invention care must be taken to assure that the particulate materials are dispersed relatively uniformly throughout the composition.

Creams of this invention may be packed in conventional antiperspirant cream containers known in the art. Such packages typically contain the cream in bulk form. The cream is then applied by hand, or by a pad or similar applicator device. The creams of the present invention may also be packed in a dispenser designed to extrude or otherwise directly apply the creams to the skin.

The antiperspirant cream compositions of the present invention are utilized in a conventional manner to treat or prevent perspiration on areas of the human body, such as the axillary areas, which are prone to perspiration wetness. Specifically, an effective amount of any of the compositions described herein is applied topically to such areas one or more times a day. When this is done, the compositions provide effective antiperspirant performance, as well as reduced residue on the skin, and good aesthetics upon application for the user.

The following non-limiting examples illustrate the compositions, processes of manufacture, and methods of use described in the present application.

EXAMPLE I

An antiperspirant cream composition of the present invention is prepared as follows.

| Component | Weight % |
| --- | --- |
| Cyclomethicone D-5[1] | 30.5 |
| Permethyl 101A[2] | 15.0 |
| Permethyl 102A[3] | 15.0 |
| Propylene Carbonate[4] | 1.6 |
| Quaternium-18 (Ditallow dimethyl ammonium chloride) Hectorite[5] | 6.0 |

| Component | Weight % |
| --- | --- |
| Castor Wax[6] | 3.7 |
| Polyethylene Spheres[7] | 5.5 |
| Aluminum Zirconium Trichlorohydrex Gly[8] | 22.7 |
| | 100% |

[1] A cyclic polydimethylsiloxane containing 5 carbons, supplied by G. E. Silicones
[2] 16 carbon branched chain hydrocarbon fluid, supplied by Permethyl Corporation (density = 0.79 g/cm$^3$; b.p. = 210-250° C.)
[3] 20 carbon branched chain hydrocarbon fluid, supplied by Permethyl Corporation (density = 0.83 g/cm$^3$, bp = 275-300° C.)
[4] Supplied by Texaco
[5] Bentone-38, supplied by NL Industries
[6] Thixin E, supplied by NL Industries
[7] Microthene ML-733, supplied by U.S. Industrial Chemicals
[8] Supplied by Westwood Chemical Corporation All of the ingredients except the propylene carbonate are combined and heated to 49° C. (120° F.) with agitation. The propylene carbonate is then slowly added to the batch while milling with a Tekmar mill. The resulting stiff cream is filled into jars or cream applicators and allowed to cool. The penetration force value of the composition is about 118 grams.

EXAMPLE II

The following is an antiperspirant cream composition of the present invention.

| Component | Weight % |
| --- | --- |
| Cyclomethicone D-5 | 40.5 |
| Permethyl 103A[1] | 20.0 |
| Propylene Carbonate | 2.0 |
| Quaternium-18 Hectorite | 7.5 |
| Talc | 5.0 |
| Aluminum Chlorohydrate[2] | 25.0 |
| | 100% |

[1] 24 carbon branched chain hydrocarbon fluid, supplied by The Permethyl Corporation (density = 0.838 g/cm$^3$ b.p. = 230-350° C.)
[2] Dow Corning ACH-323 impalpable powder, supplied by Dow Corning This cream composition is prepared in a manner similar to the cream described in Example I, except that for this composition no heating is required.

EXAMPLE III

The following is an antiperspirant cream composition of the present invention.

| Component | Weight % |
| --- | --- |
| Cyclomethicone D-5 | 36.7 |
| Light Mineral Oil[1] | 10.0 |
| Permethyl 101A | 10.0 |
| Propylene Carbonate | 1.8 |
| Quaternium-18 Hectorite | 7.0 |
| Castor Wax | 4.5 |
| Aluminum Chlorohydrate | 30.0 |
| | 100% |

[1] Benol White Mineral Oil, supplied by Witco Chemical Corp. (viscosity = 18-20 csk at 40° C.; density = 0.839-0.855 g/cm$^3$)

This cream composition is prepared by essentially the same procedure as described in Example I.

The antiperspirant compositions described in Examples I-III, when applied to the axillary area of the user, provide effective prevention and control of perspiration wetness. These compositions are stable, have excellent aesthetics, and provide reduced visible residue on the skin after application.

What is claimed is:

1. An antiperspirant cream composition, having a penetration force value of from about 60 grams to about 500 grams, comprising:
    (a) from about 20% to about 70% of a volatile silicone material;
    (b) from about 5% to about 35% of a particulate antiperspirant active;
    (c) from about 3% to about 10% of a clay thickening agent;
    (d) from about 0.1% to about 5% of an activator for said clay thickening agent; and
    (e) from about 5% to about 40% of a non-volatile paraffinic hydrocarbon fluid, said non-volatile paraffinic hydrocarbon fluid being mineral oil.

2. An antiperspirant cream composition according to claim 1 which comprises from about 8% to about 25% of the non-volatile paraffinic hydrocarbon fluid.

3. An antiperspirant cream composition according to claim 1 which comprises from about 20% to about 50% of the volatile silicone material.

4. An antiperspirant cream composition according to claim 1 wherein the volatile silicone material is a cyclic silicone having the formula

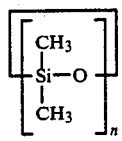

wherein n is from about 3 to about 7.

5. An antiperspirant cream composition according to claim 4 wherein the particulate antiperspirant active is selected from the group consisting of ZAG complexes, and actives having the formula

wherein a is from about 2 to about 5, a+b is about 6, x is from about 1 to about 6, and wherein a, b, and x may have non-integer values, and mixtures thereof.

6. An antiperspirant cream composition according to claim 5 wherein the clay thickening agent is selected from the group consisting of hydrophobically-treated bentonites, hydrophobically-treated hectorites, and mixtures thereof.

7. An antiperspirant cream composition according to claim 6 wherein the activator is selected from the group consisting of propylene carbonate, ethanol, methanol and mixtures thereof.

8. An antiperspirant cream composition according to claim 1 which additionally comprises from about 0.5% to about 5% of a non-clay thickener.

9. An antiperspirant cream composition according to claim 8 wherein the non-clay thickener is castor wax.

10. A method for treating and preventing perspiration in humans comprising the topical application to the axillary area of an effective amount of the antiperspirant cream composition according to claim 1.

* * * * *